(12) United States Patent
Lavery et al.

(10) Patent No.: US 6,398,740 B1
(45) Date of Patent: Jun. 4, 2002

(54) APPARATUS AND METHOD FOR MONITORING THE TEMPERATURES ON THE PLANTAR ASPECTS OF A HUMAN FOOT AND OTHER VITAL HEALTH INFORMATION

(75) Inventors: Lawrence A. Lavery; Mauli Agrawal; Kyriacos A. Athanasiou; George P. Constantinides; Dan R. Lanctot; Ruben G. Zamorano, all of San Antonio, TX (US)

(73) Assignee: Salix Medical, Inc., San Antonio, TX (US)

( * ) Notice: Subject to any disclaimer, the term of this patent is extended or adjusted under 35 U.S.C. 154(b) by 0 days.

(21) Appl. No.: 09/578,948

(22) Filed: May 25, 2000

(51) Int. Cl.$^7$ ............................. A61B 5/00; A61B 5/103; A61B 5/117

(52) U.S. Cl. ...................... 600/549; 600/592; 600/300; 600/301; 128/903; 128/904; 374/112

(58) Field of Search ................................ 600/300–301, 600/549, 587–592, 474; 128/903, 904, 900; 374/110–119; 73/172; 36/136

(56) References Cited

U.S. PATENT DOCUMENTS 5,642,096 A * 6/1997 Leyerer et al. ............. 600/592
6,080,106 A * 6/2000 Lloyd et al. ................ 600/300

* cited by examiner

Primary Examiner—Eric F. Winakur
Assistant Examiner—Michael Astorino
(74) Attorney, Agent, or Firm—Jenkens & Gilchrist, A Professional Corporation

(57) ABSTRACT

An apparatus and method for monitoring items of vital health information including temperature of the plantar aspects of the foot of the human, body weight, blood pressure, pulse rate, blood glucose level and blood oxygen level. The apparatus includes a platform on which the user stands. Included on the platform are a set of heat sensitive signal generating devices. The temperature at predetermined locations on the plantar aspects of the human foot are determined by the signals obtained from the individual heat sensitive, signal generating probes. Other items of vital health information may be obtained by other sensors on the apparatus.

30 Claims, 3 Drawing Sheets

APPARATUS AND METHOD FOR MONITORING THE TEMPERATURES ON THE PLANTAR ASPECTS OF A HUMAN FOOT AND OTHER VITAL HEALTH INFORMATION

FIELD

The present invention pertains to a monitoring apparatus; more particularly, the present invention pertains to an apparatus and method for monitoring the temperatures on different predetermined locations on the plantar aspects of a human foot as well as other vital information indicative of the health of a human being.

BACKGROUND

Many conditions which have a negative impact on the health of a human being are preceded by small changes in measurable parameters such as temperature, weight, or blood pressure. For example, a significant weight gain may be indicative of fluid retention. And fluid retention and/or an increase in blood pressure may be predictive of severe heart problems.

Afflictions of the lower extremities can also be predicted by a change in the temperatures on the bottom of the feet. In the United States alone, it is estimated that up to 16,000,000 people suffer from diabetes and approximately 60–70% of these diabetics will develop foot-related medical problems sometime during their lifetime. Of all diabetes-related hospitalizations, 20% of these hospitalizations are for foot-related complications. The number of hospitalizations can be reduced if medical personnel are forewarned of significant changes in the temperatures on the bottom of the feet. For example, it is well known that skin temperatures on the bottom of a person's feet will increase before ulceration.

Foot problems are particularly problematic for diabetics because diabetics often lose sensation in their feet. This loss of sensation the feet often leads to ulceration. In extreme cases the ulceration may eventually lead to an amputation of the diabetic's foot. The foot problems typically associated with the disease of diabetes often cause immense pain and suffering. Such pain and suffering significantly diminishes the quality of life for a diabetic. In addition, these foot problems substantially increase the diabetic's health care cost. There is therefore a need in the art for a device which facilitates the monitoring of foot temperatures and provides an early warning of any significant temperature differences between the two feet. Such foot temperature monitoring may provide an early indication conditions which can lead to neuropathy, ulceration, infection, wound healing problems, fracture, and even amputation.

In yet another area, changes in blood pressure at various locations on the human body may be indicative of reduced blood flow. Such reduced blood flow may lead to significant reduction in the health of the affected body part.

In yet still another area, changes in blood chemistry may be indicative of nascent problems which are not yet symptomatic.

Thus, there is a significant need to develop a device to facilitate the monitoring of other vital health information to include weight and blood pressure. Such monitoring of other vital information may provide an early indication of conditions which can lead to future heart problems.

SUMMARY

The present invention facilitates the monitoring of vital health information to include the temperature on the bottoms of a person's feet, body weight, and blood pressure. This monitoring of vital health information is accomplished by an apparatus which is built around a system for monitoring the temperature at different locations on the plantar aspects of the foot of a human being, particularly a diabetic.

In the preferred embodiment of the invention a platform includes an array of force or pressure sensors. The output of the array of force or pressure sensors provides an indication of the position of a person's feet on the platform. The platform also includes a set of heat sensitive, signal generating probes. Once the force or pressure sensors have provided an indication of the position of the person's feet on the platform, the heat sensitive signal generating probes at predetermined locations under the patient's feet are activated. These heat sensitive, signal generating probes sense the temperature at predetermined locations on the planar aspects of both the left foot and the right foot. The activation of the temperature sensing probes results in the production of an electrical signal representative of the different temperatures on each of the patient's feet. If there is a significant difference between the temperatures on the left foot and the right foot, an alarm signal can be provided to the user. The electrical signals can also be displayed to the user as a temperature reading, stored for future use, or sent to a central monitoring facility.

In the preferred embodiment, the output of the force or pressure sensors is also used to monitor the patient's weight. If desired, a blood pressure cuff and pulse monitor may also be used. The blood pressure cuff may be placed at heart level on the user's arm or an additional cuff may be placed around the user's ankle or the user's toe.

Once other vital health information has been sensed, that information may be compared to previously sensed vital health information. For example, a comparison of a patient's weight to prior readings may reveal a weight gain predictive of congestive heart failure. Similarly, significant differences in blood pressure readings may be predictive of future cardiovascular problems.

All of the sensed vital health information may be displayed to the user or transmitted by telephone or other commonly used wireless communication systems to a central facility where medical professionals can determine if the sensed conditions are predictive of future medical problems. If desired, the apparatus itself may produce alarms of particularly dangerous conditions. For example, if the difference in the temperatures sensed on the bottom of the left foot and the bottom of the right foot or if the patient's blood pressure is above a certain level, an audible signal or a visual message can be generated.

BRIEF DESCRIPTION OF THE FIGURES

A better understanding of the apparatus and method for monitoring the temperature on the planar aspects of a human foot and other vital health information may be had by reference to the drawings, wherein.

DESCRIPTION OF THE EMBODIMENTS

Figure 1:
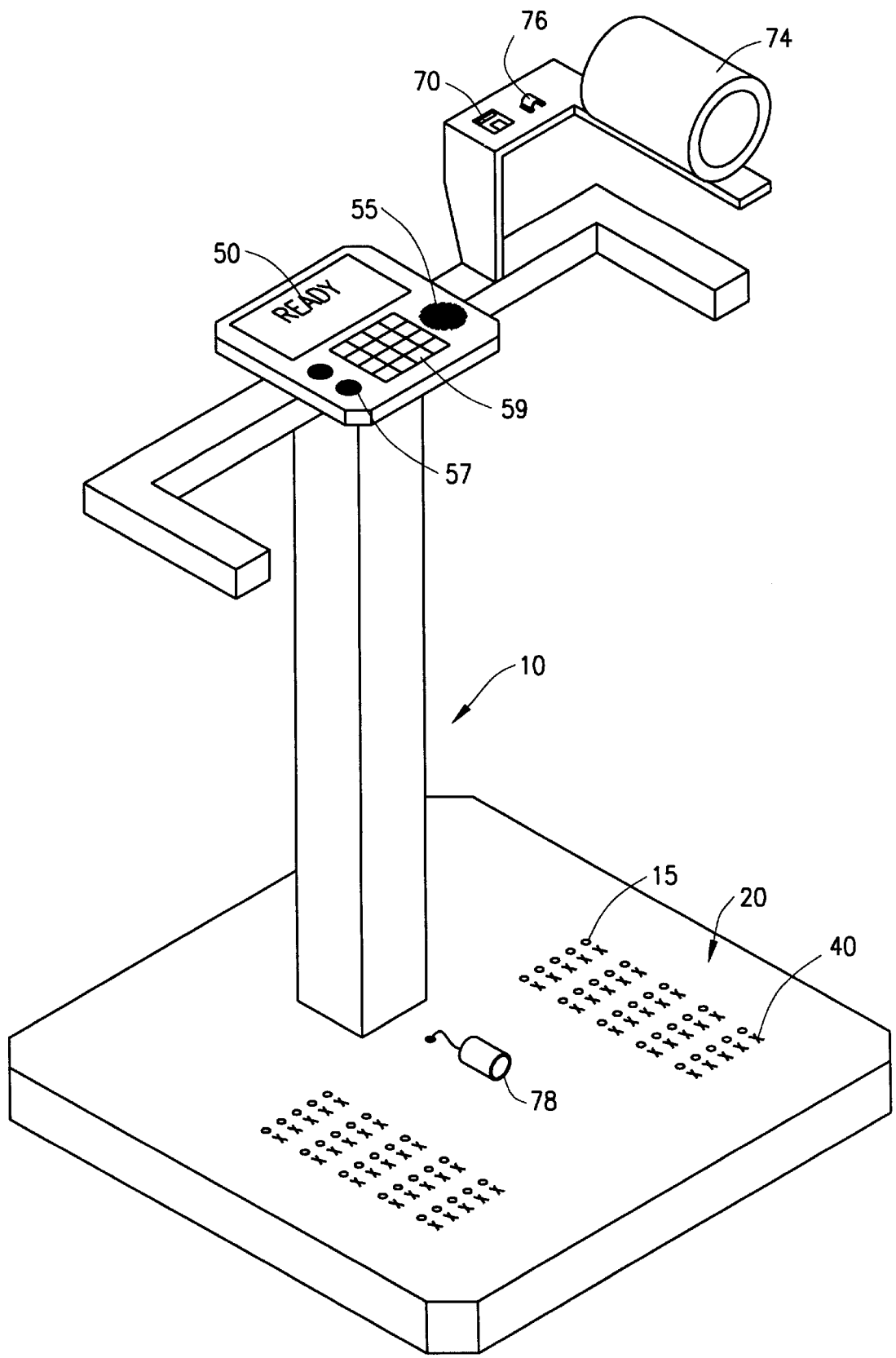
FIG. 1 is a perspective view of the preferred embodiment of the present invention.

As may be seen in FIG. 1, the preferred embodiment of the apparatus 10 for monitoring vital health information to include the temperature of the plantar aspects of the human foot, body weight, and blood pressure is designed for use either in the patient's home or in health care facilities. It is expected that the patients who would receive the greatest benefit from the apparatus are diabetics who are at high risk for developing medical complications on their lower extremities, particularly their feet.

The preferred embodiment of the present invention 10 allows the patient to obtain a quick scan of the temperatures on the plantar aspects of both feet, body weight, and blood pressure. In a less expensive embodiment 110 as shown in FIG. 2, the capabilities to monitor either body weight or blood pressure are eliminated.

The quick scan of foot temperatures allows the monitoring of differences in temperatures between the left foot and the right foot or the monitoring of foot temperatures at different locations on the patient's foot over time. Variations in foot temperatures often signal conditions which are predictive of inflammation or ulceration and which conditions, if left untreated, may lead to eventual amputation of an entire lower extremity.

Figure 2:
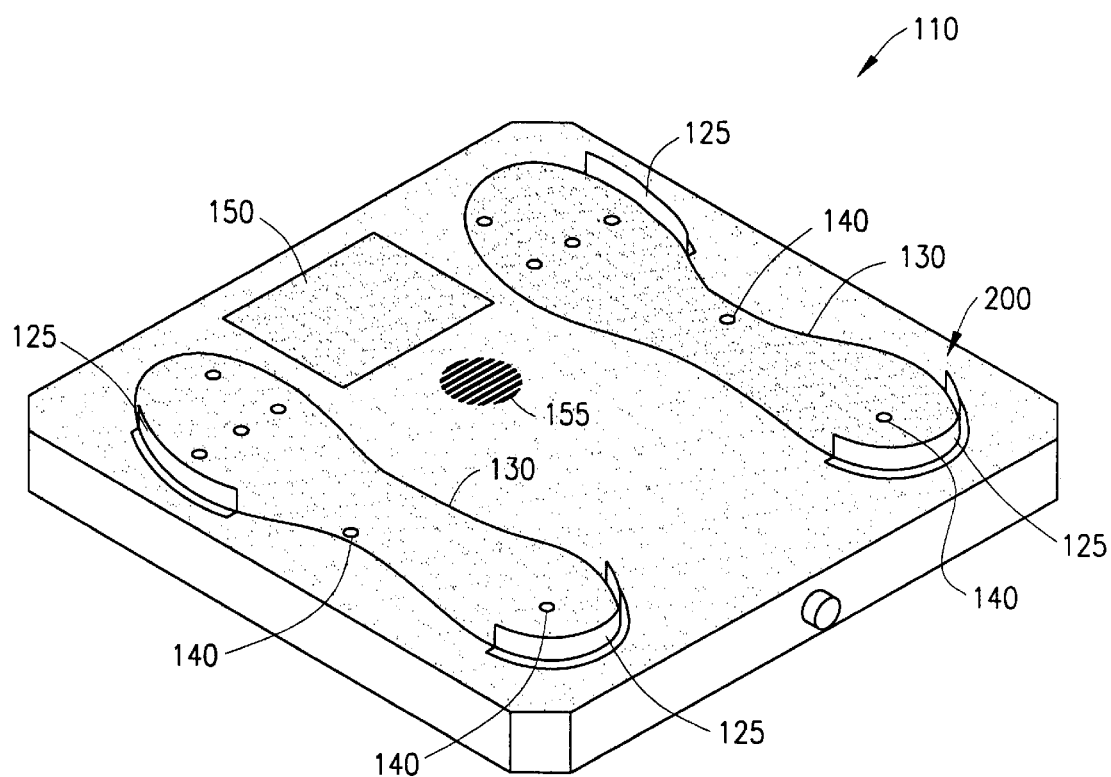
FIG. 2 is a perspective view of the platform which is used to measure the temperatures on the plantar aspects of the user's feet.

As shown in FIG. 1 and FIG. 2, the apparatus of the present invention 10, 110 is not unlike a commonly used bathroom scale for determining body weight. Specifically, the user is instructed to first step on the platform 20. In the embodiment shown in FIG. 1 an array of pressure sensitive transducers 15 in the platform 20 detect the position of the user's foot by locating those portions of the foot which bear the weight of the body such as the heel and ball of the foot. Once the force signals provide an indication of foot position, the temperatures at preselected sites on the bottom or plantar aspects of both feet are measured. The device 10 will alert the user if there is an abnormally high temperature gradient between the plantar aspects of the contra lateral feet. The presence of such a significant temperature gradient may be indicative of a pathologic inflammation or possible tissue damage at that location on the user's foot. Such inflammation or tissue damage might be an indicator of a predisposition to further tissue breakdown in the foot and/or significant morbidity which, if left untreated, may lead to an amputation or, in extreme cases, death.

As shown in FIG. 1 and FIG. 2, the apparatus of the present invention 10, 110 is built around a platform assembly 20 that is placed on a hard surface (not shown). Two pads or foot guides 130 may be used to guide the placement of the patient's feet. These foot guides 30 assure that the patient places his feet reproducibly and accurately on the platform assembly 20. Each foot guide 130 assures proper registration of the patient's foot with respect to a set of commonly available temperature sensing transducers 140. For patients with unusually shaped or deformed feet, custom made foot guides may be used.

In the preferred embodiment shown in FIG. 1 pressure sensitive transducers 15 determine the location of the user's feet on the platform 20. This location information is then used to activate temperature sensing transducers 40 at pre-determined locations.

The temperature sensing transducers 40, which provide an electrical signal representative of a temperature level, are disbursed on top of the platform assembly 20. These electrical signals are then displayed as either Fahrenheit or Celsius temperature readings to the user.

If desired a liquid crystal display 50, 150 can either show the actual temperature values measured by one or more temperature sensitive transducers 40, 140 and/or alert the user that a difference in temperature may exist between two sensor sites. Alternatively, the temperature readings or warnings about possibly dangerous temperature differences may be conveyed audibly to the user through one or more speakers 55, 155.

It has also been found that the utility of the apparatus 10 for monitoring the temperature of the plantar aspects of the human foot can be expanded to measure other vital health information through the use of a variety of different enhancements. Specifically, the apparatus of the present invention 10, 110 can easily be modified to also measure the weight of the patient. The measurement of weight is important because fluctuations in weight may be significant to patients in the early stages of congestive heart failure. Such sudden weight change usually signifies water retention in the chest cavity. The need to monitor fluctuations in weight is particularly important for diabetics who are prone to suffer from congestive heart failure. Thus, it is desirable for diabetics that the foot temperature variations and body weight changes be quantified and displayed on a daily basis. Selection of the health information displayed is facilitated by the use of easily accessible buttons 57 or a keypad 59 as shown in FIG. 1.

If desired, body weight may be measured with the apparatus 10, 110 using a force or pressure transducer 15 in the same way that force or pressure transducers are used in standard bathroom scales. The liquid crystal display 50, 150 may be used for the display of body weight.

It has also been found that the preferred embodiment of the apparatus 10 of the present invention may be further enhanced by the addition of still other medical condition monitoring systems well known to those of ordinary skill in the art. Such other medical condition monitoring systems may measure blood glucose levels with a finger pin stick system 70, an arm blood pressure cuff and pulse counter 74, or a red light and light sensor clipped on the end of a finger to measure blood oxygen 76. Present technology enables the measurement of blood glucose levels and blood oxygen using a variety of techniques including lasers, infrared percutaneous readings or assessment of blood glucose levels using the patient's saliva. Blood pressure may even be measured at foot level with an ankle cuff or toe cuff 78.

Once the vital health information has been obtained by the apparatus 10 of the present invention, it may be stored internally where it can be compared with prior data to inform the user of noticeable trends in changes of weight or temperature and, if necessary, provide an alarm signal. Alternatively, the information may sent to a central computer using a standard telephone system 80, the internet, cell phone, or other wireless communication means. The central computer 100 monitors the measurements of vital health information taken by the device 10, 110 and thereby allows such measurements to be taken by patients in the comfort of their own home.

Figure 3:
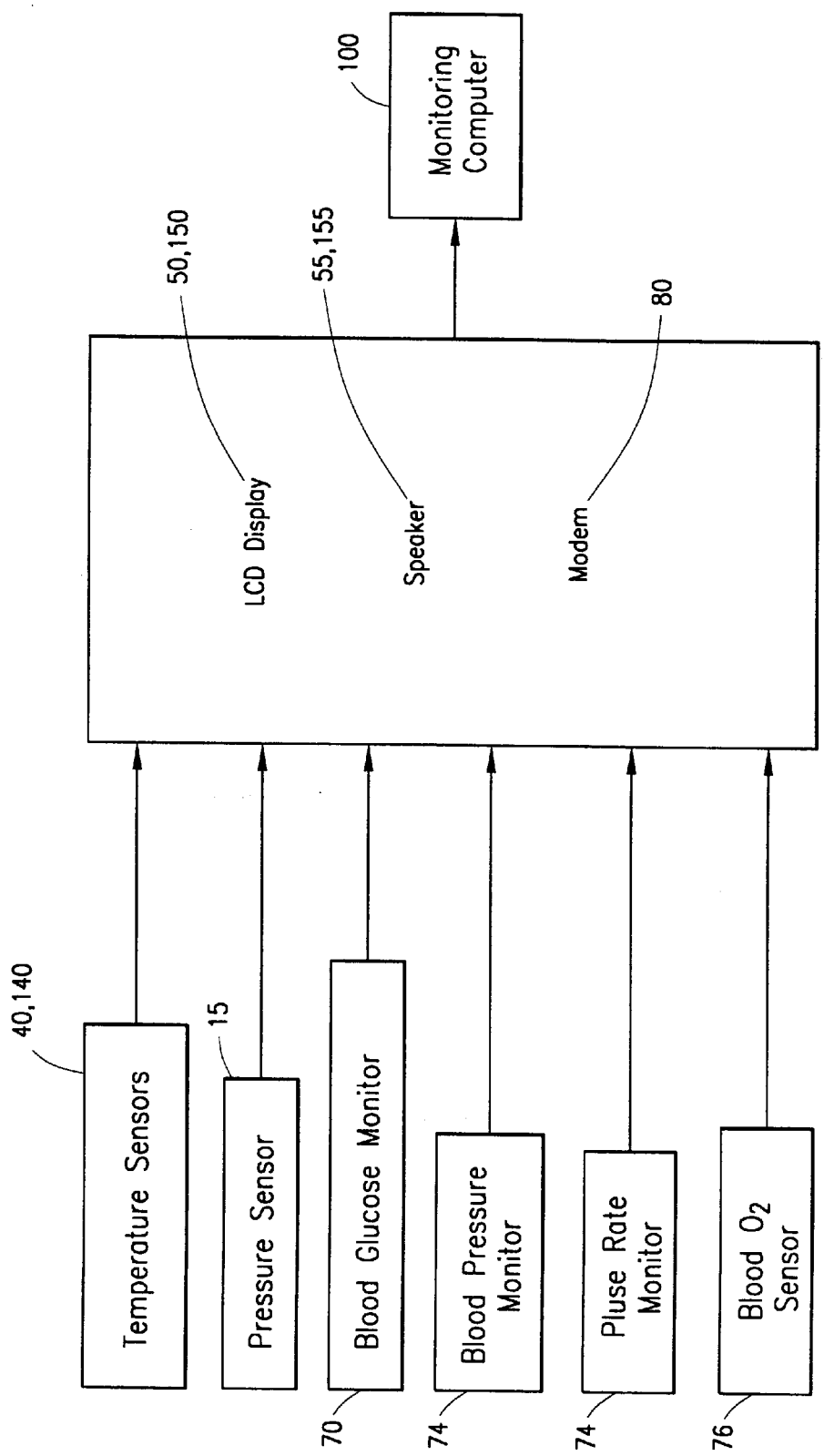
FIG. 3 is a schematic diagram of the interrelationship of the main components of the present invention.

The schematic diagram of FIG. 3 shows how the various components of the device of the present invention are interconnected.

Operation

The present invention may be utilized if the patient is either lying down, sitting, or standing up. The key aspect of the present invention is to ensure that the bottom of the patient's feet are properly registered with respect to the array of temperature sensitive transducers 40 located in the platform assembly 20. Alternatively, foot temperatures could be measured by non-contact means such as infra-red probes or by the use of thermal imaging techniques.

In the low cost embodiment shown in FIG. 2, the proper registration of each foot with respect to the array of probes may be accomplished by the use of simple guides 125 which surround the array of temperature sensitive transducers 140. These simple guides may be pre-located by medical personnel for an individual patient and preferably include a heel plate and a side plate against which the patient may rest his/her foot.

If it is necessary to measure the temperature variations in a persons' foot while the person is in a hospital bed or in an ambulance, portable pads which contain the temperature sensitive transducers may be strapped into proper position on the user's foot. In yet another alternative embodiment, the temperature sensitive transducers may actually be placed in a pad which is insertable into a shoe. Connections from temperature sensitive transducers 40 would then lead to a plug-in connection on the patient's shoe. The data sent by the temperature sensitive transducers could then be sent from the shoe by merely plugging in a connector at a convenient location on the shoe—which connector is connected to individual temperature sensitive transducers. The foot temperature data could be sent to a central monitoring facility 100 using wireless or cellular telephone techniques.

In yet another embodiment the data collected by the apparatus 10, 110 will include an indication of the date and time the temperature readings were taken. This data may be stored at the device 10, 110 itself or transmitted to a remote location by wireless means where it may be stored and later analyzed.

If the data is transmitted to a database at a remote location, it would then be possible for a health care professional to monitor the data and determine if a significant change has occurred in the contra lateral temperatures of a user's lower extremities, the user's weight, or the user's blood pressure.

The apparatus and method of the present invention may also provide the foundation for a method of operating a health information monitoring business. Specifically, the sensed vital health information could be sent to a data storage facility and compared with past data or predetermined levels of vital health information. If this comparison yields an indication of a condition which is predictive of future health problems, a health care professional may call the patient and recommend a consultation or treatment which may cure a nascent condition before life or limb-threatening symptoms are experienced. Such a vital health information monitoring system could be required for use by designated employees of an employer to reduce lost time maladies. Further, such a vital health information monitoring system could also be required for use by life or health insurance companies to provide a basis for reassessing the risk that the insurance company will have to pay for the health care costs associated with an illness or malady or the face amount of a life insurance policy on the death of the insured. Such risk reassessment could be used to tailor premium rates to the health of individual insureds.

It will be understood by those of ordinary skill in the art that while the apparatus and method of the present invention has been described with respect to its preferred embodiment, those of ordinary skill in the art will understand the numerous other embodiments of this invention may be possible without departing from the foregoing teachings. Such other embodiments shall be included within the scope and meaning of the appended claims.

What is claimed is:

1. An apparatus for monitoring temperature of the plantar aspects of the foot of a human being, said device comprising:

a platform;

an array of force sensitive devices for determining the location of the left foot on the platform;

an array of force sensitive devices for determining the location of the right foot on the platform;

a set of temperature sensitive, signal generating devices located in the platform;

said force sensitive devices and said temperature sensitive, signal-generating devices being interconnected to activate a subset of said temperature sensitive, signal generating devices at predetermined locations under the human being" feet;

means for converting said signals generated by said temperature sensitive devices into an output expressed in terms of temperature.

2. The apparatus as defined in claim 1 further including means for generating a warning if a temperature beyond a predetermined level as between two or more of said temperature sensitive devices is sensed.

3. The apparatus as defined in claim 1 wherein said output of sensed temperatures is a visual output.

4. The apparatus as defined in claim 3 wherein said visual output is a liquid crystal display.

5. The apparatus as defined in claim 1 wherein said output of sensed temperatures is an audio output.

6. The apparatus as defined in claim 1 further including means for sensing and displaying the weight of the human being.

7. The apparatus as defined in claim 1 further including means for sensing and displaying the blood pressure of the human being.

8. The apparatus as defined in claim 1 further including means for sensing and displaying the pulse rate of the human being.

9. The apparatus as defined in claim 1 further including means for sensing and displaying the blood glucose levels of the human being.

10. The apparatus as defined in claim 1 further including means for sensing and displaying the blood oxygen levels of the human being.

11. The apparatus as defined in claim 1 further including a modem for transmitting the sensed foot temperatures to a remote location.

12. The apparatus as defined in claim 7 further including means for transmitting the sensed blood pressure to a remote location.

13. The apparatus as defined in claim 8 further including means for transmitting the sensed pulse rate to a remote location.

14. The apparatus as defined in claim 9 further including means for transmitting the sensed blood glucose level to a remote location.

15. The apparatus as defined in claim 10 further including means for transmitting the sensed blood oxygen level to a remote location.

16. A system for monitoring the temperatures of the plantar aspects of the feet of a plurality of patients, each of said patients having different size feet, said system comprising:

plurality of individual foot temperature measuring devices, each of said plurality of individual foot temperature measuring devices including:

a platform means for determining the location of the left foot on said platform;

means for determining the location of the right foot on said platform;

a set of heat sensitive, signal generating probes constructed and arranged on said platform to sense the heat levels at predetermined locations on both the left foot and the right foot of the human being, said predetermined locations being activated by said means for determining the location of the left foot on the platform and said means for determining the location of the right foot on the platform;

means for converting said signals generated by said heat sensitive probes into an output expressed in terms of temperature;

means for sending signals to a remote location;

means for storing and analyzing said signals at said remote location;

whereby the temperatures of the feet of a plurality of human beings may be measured at said remote location.

17. The system as defined in claim 16 wherein said means for sending said signals to a remote location is a telephone modem.

18. The system as defined in claim 16 further including means for generating a warning if a temperature beyond a predetermined level as between two or more of said probes is sensed.

19. The system as defined in claim 16 further including a visual display of sensed temperatures.

20. The system as defined in claim 18 further including means for generation of an audio warning.

21. The system as defined in claim 16 further including means for sensing and displaying the weight of the human being.

22. The system as defined in claim 16 further including means for sensing and displaying the blood pressure of the human being.

23. The system as defined in claim 16 further including means for sensing and displaying the pulse rate of the human being.

24. The system as defined in claim 16 further including means for sensing and displaying the blood glucose levels of the human being.

25. The system as defined in claim 16 further including means for sensing and displaying the blood oxygen levels of the human being.

26. The system as defined in claims 16, 21, 22, 23, 24 and 25 further including means for storing the sensed information along with the date and time when the information was sensed.

27. A health monitoring system comprising:

a left footpad and a right footpad;

each of said left footpad and said right footpad including:
   means for determining the location of the plantar aspects of the left and right foot on said left and right foot respectively;
   a plurality of individual temperature sensors to be activated at predetermined locations on said left footpad and said right footpad under said plantar aspects of said left and right foot by said means for determining the location of the left foot and the right foot;
   whereby the temperature at predetermined locations on the plantar aspects of the feet of a human being may be repeatedly measured.

28. The health monitoring system as defined in claim 27 further including means for securing said left foot pad and said right foot pad to the feet of the patient.

29. The health monitoring system as defined in claim 28 wherein said left foot pad and said right foot pad are tailored to fit an individual patient.

30. A method for monitoring the temperature at predetermined locations on the feet of a human being, said method comprising the steps of:

determining the location of the feet with respect to a pad;

activating a plurality of temperature sensors at locations in said pad said temperature sensor locations being determined by the location of the feet with respect to said pad;

placing said pad against the bottom of the foot of a patient so that said activated temperature sensors are repeatedly in contact with the same locations on the bottom of the patient's foot.

* * * * *